United States Patent [19]

Miwa et al.

[11] 4,139,572

[45] Feb. 13, 1979

[54] 1-ALKYL-4-ISOPROPYLBENZENE DESORBENTS FOR PARA-XYLENE

[75] Inventors: Kishio Miwa, Kamakura; Takehisa Inoue, Tokyo; Kazuo Tsunoi, Kamakura, all of Japan

[73] Assignee: Toray Industries, Inc., Tokyo, Japan

[21] Appl. No.: 825,562

[22] Filed: Aug. 18, 1977

Related U.S. Application Data

[63] Continuation of Ser. No. 816,945, Jul. 19, 1977, abandoned.

[30] Foreign Application Priority Data

Aug. 30, 1976 [JP] Japan ................................ 51-102567

[51] Int. Cl.$^2$ .............................................. C07C 7/13
[52] U.S. Cl. ............................................. 260/674 SA
[58] Field of Search .................................. 260/674 SA

[56] References Cited

U.S. PATENT DOCUMENTS

| | | | |
|---|---|---|---|
| 3,686,342 | 8/1972 | Neuzil | 260/674 SA |
| 3,761,533 | 9/1973 | Otani et al. | 260/674 SA |
| 3,903,187 | 9/1975 | Geissler | 260/674 SA |
| 3,943,184 | 3/1976 | Rosback | 260/674 SA |

*Primary Examiner*—Delbert E. Gantz
*Assistant Examiner*—C. E. Spresser
*Attorney, Agent, or Firm*—Miller & Prestia

[57] ABSTRACT

Para-xylene is selectively adsorbed from a $C_8$ aromatic hydrocarbon feed by a crystalline selective adsorbent, and then the para-xylene is subsequently desorbed by contacting the resulting adsorbent with a 1-(lower alkyl)-4-isopropylbenzene desorbent, wherein the lower alkyl group contains one to two carbon atoms. The desorbent effectively desorbs the para-xylene from the adsorbent, and the para-xylene may be produced as an enriched product.

21 Claims, 1 Drawing Figure

1-ALKYL-4-ISOPROPYLBENZENE DESORBENTS FOR PARA-XYLENE

This Application is a continuation of Application Ser. No. 816,945, filed on July 19, 1977, now abandoned.

SUMMARY OF THE INVENTION

Para-xylene may be separated from a mixture containing it and other $C_8$ aromatic hydrocarbons through selective adsorbents, including those disclosed in U.S. Pat. No. 3,761,533, Otani et al granted Sep. 25, 1973, and assigned to Toray Industries, Inc. Otani et al disclose the advantageous use of certain crystalline metal alumino-silicate sorbents (column 10, line 49—column 12, line 47). These sorbents may be used for the selective adsorption of para-xylene.

The present invention provides an improved process and desorbent for the para-xylene, wherein the desorbent comprises a 1-(lower alkyl)-4-isopropylbenzene wherein the lower alkyl group containing 1–2 carbon atoms. The desorbents, thus, comprise either para-cymene or 1-ethyl-4-isopropylbenzene.

In a preferred embodiment, the initial separation of the para-xylene through adsorption is conducted with the use of a faujasite type zeolite containing potassium cations as disclosed in the aforementioned Otani et al patent. The faujasite type zeolite should contain individual potassium cations at the cation exchangeable sites.

Optionally, in accordance with a more specific embodiment of this invention, the faujasite type zeolite may also contain, in addition to the potassium cations, Group IA cations other than potassium, or Group IIA, Group IB, yttrium, lead, zirconium, neodymium, thallium, thorium or proton.

The desorbent of the invention may in one embodiment consist essentially of 1-($C_{1-2}$ alkyl)-4-isopropylbenzene together with other aromatic hydrocarbons, such as isomers of para-cymene, isomers of 1-ethyl-4-isopropylbenzene and diethylbenzenes.

In a more specific embodiment, the 1-($C_{1-2}$ alkyl)-4-isopropyl benzene may be used in admixture with one or more saturated hydrocarbons, such as paraffins, particularly cycloparaffins, and more particularly decahydronaphthalene.

DETAILED DESCRIPTION OF THE INVENTION

Figure 1:
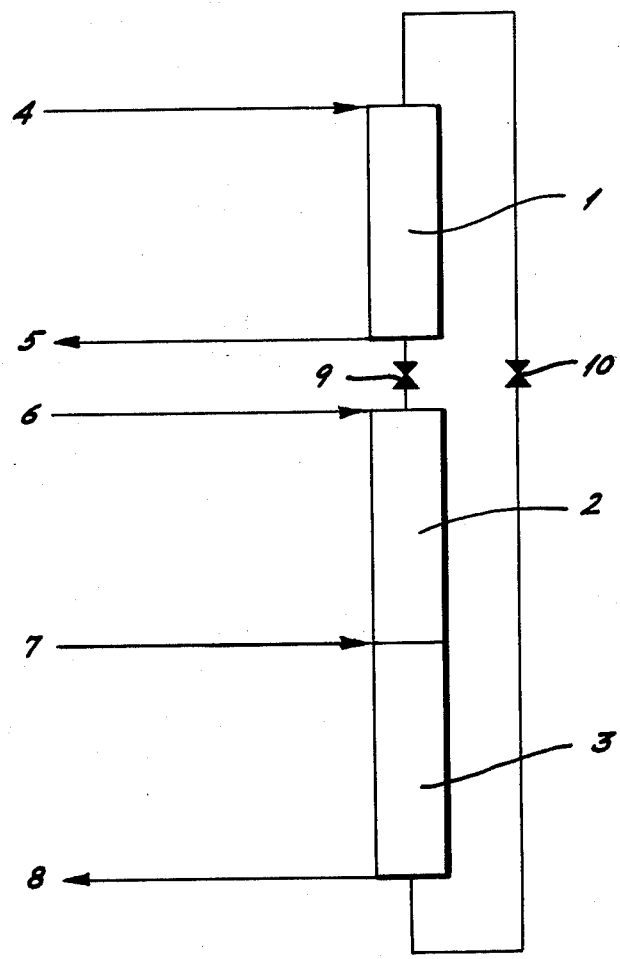

The present invention relates to an improved process for separation of para-xylene from a feed containing a mixture of $C_8$ aromatic hydrocarbons by adsorptive separation techniques such as disclosed in the Otani et al patent, where the paraxylene is selectively adsorbed from the feed by a crystalline adsorbent. More particularly, the invention relates to the discovery of surprisingly active agents for desorbing paraxylene from a crystalline adsorbent, preferably a crystalline aluminosilicate adsorbent and thereby sharply separating para-xylene from a mixture of $C_8$ aromatic hydrocarbons containing para-xylene.

The phrase "$C_8$ aromatic hydrocarbons" is intended to designate a mixture which includes at least one other eight-carbon aromatic hydrocarbon in addition to the desired para-xylene. Such other hydrocarbon may be meta-xylene, ortho-xylene or ethylbenzene, for example. According to this invention it is possible with surprising effectiveness to separate para-xylene from a mixture containing one or several other C8 aromatic hydrocarbons.

Some of the manipulative steps of the adsorptive separation process are disclosed in Otani et al and also in U.S. Pat. Nos. 3,686,342 and 3,626,020. Although the adsorptive step has been found to remove the para-xylene from the $C_8$ aromatic hydrocarbon feed by adsorbing the para-xylene onto the crystalline aluminosilicate adsorbent, the problem remains as to how then to desorb the para-xylene, which is the desired product.

It has now been disclosed that, through the use of a 1-($C_{1-2}$ alkyl) isopropylbenzene desorbent, an improved result in the overall process is achieved, as compared to the Otani process.

The process is carried out stepwise on the adsorbent, with alternating steps of adsorption and desorption repeated indefinitely. Accordingly, in the adsorption step, the $C_8$ aromatic feed is contacted with an adsorbent in which some of the previously used desorbent material remains. Para-xylene is selectively adsorbed on the adsorbent, displacing a part of the remaining desorbent, and a raffinate material is produced which includes the less selectively adsorbed components of the feed. The raffinate is removed, together with the displaced desorbent, which is a 1-($C_{1-2}$ alkyl)-4-isopropylbenzene.

In the desorption step, the selectively adsorbed para-xylene remaining on the crystalline adsorbent is displaced by contacting the adsorbent with a 1-($C_{1-2}$ alkyl)-4-isopropylbenzene desorbent. There thus remains an extract which includes the 1-($C_{1-2}$ alkyl)-4-isopropylbenzene desorbent, and para-xylene.

There are several requirements which are significant in evaluating the quality of a desorbent. The desorbent material must be capable of displacing para-xylene from the crystalline adsorbent, and it also must be a compound which can be readily separated from para-xylene. The pore diameter of the adsorbent utilized is at least 5.6 angstroms. Preferably, the pore diameter of the adsorbent is in the range of 5.6–10.0 angstroms.

A second general requirement is that the desorbent must be capable of being displaced from the crystalline adsorbent by the para-xylene of the feed itself, to permit the use of a continuous process. If this characteristic is lacking in the desorbent, it would not be possible to practice a continuous process with the feed itself serving to displace the desorbent.

It should also be noted that this process involves a competitive adsorption of para-xylene by the desorbent. As mentioned above, para-xylene is adsorbed on the crystalline adsorbent, which contains residual desorbent, and thus displaces a part of the remaining desorbent. It is therefore a significant characteristic of the desorbent material that is used in such a separation process that it should not significantly interfere with the selective adsorptive capability of the crystalline adsorbent.

In determining the adsorptive capability of a particular adsorbent one must consider the selectivity, or the alpha value of the adsorbent for para-xylene as compared with other $C_8$ aromatic hydrocarbons. Selectivity, or alpha value, may be defined for two given components as the ratio of the concentration of the two components in the adsorbed phase divided by the ratio of the same two components in the unadsorbed phase which is in equilibrium with the adsorbed phase.

The selectivity value, alpha, may be expressed in equation form as follows:

$$\alpha_{px/x} = \frac{(\text{wt. percent px/wt percent } x)_A}{(\text{wt. percent px/wt percent } x)_U}$$

wherein px is para-xylene; x is the second component; and A and U represent the adsorbed and unadsorbed phases, respectively.

When selectivity approaches unity, a condition is approached wherein there is no preferential adsorption of para-xylene. As selectivity becomes greater than unity preferential adsorption of para-xylene develops. It may therefore be seen that the greater the value of selectivity in the above equation, the better the adsorption of para-xylene versus the competing C8 aromatic hydrocarbons. A relatively small value for selectivity would considerably decrease the yield of para-xylene per unit of adsorbent, and would therefore tend toward a process which is not economical. On occasion, it may not be possible to attain the desired degree of purity of para-xylene when the desorbent provides a particularly low alpha value. A desorbent material providing relatively high value of alpha, or selectivity, as used in the foregoing equation has long been desired.

In accordance with the present invention it has been discovered that para-xylene is more effectively separated by using a 1-($C_{1-2}$ alkyl)-4-isopropylbenzene desorbent as the desorbent in a separation process which utilizes a crystalline adsorbent, the desorbent of the present invention having been found to provide a sharply and unexpectedly advantageous alpha value than para-diethylbenzene, which was previously stated (in U.S. Pat. No. 3,686,342) to be the best desorbent available for such a process.

In addition to providing a sharply better alpha value, the 1-($C_{1-2}$ alkyl)-4-isopropylbenzene desorbents of the present invention admirably meet the other requirements for desorbent material. They readily and effectively displace para-xylene, previously adsorbed on the crystalline adsorbent, so that the para-xylene can be recovered from the adsorbent and thereafter separated from the desorbent itself to provide a highly purified para-xylene product. The desorbents adsorbed in the adsorbent by displacing para-xylene are also displaced by para-xylene in the feed, so that a continuous process may be carried into effect.

The 1-($C_{1-2}$ alkyl)-4-isopropylbenzene desorbent of the present invention may be used effectively alone. However, it may alternatively be used in admixture with other compounds to provide a desorbent in accordance with the present invention. Compounds which may be used include desorbent materials of the prior art, or isomers of the instant 1-($C_{1-2}$ alkyl)-4-isopropylbenzene desorbent, such as meta-cymene, ortho-cymene, 1-ethyl-3-isopropylbenzene or 1-ethyl-2-isopropylbenzene. When the 1-($C_{1-2}$ alkyl)-4-isopropylbenzene is used in admixture with other compounds, at least a few percent (5% by weight more or less) of the 1-($C_{1-2}$ alkyl)-4-isopropylbenzene desorbent should be present. Also, whether used alone or in combination with other desorbents, the 1-($C_{1-2}$ alkyl)-4-isopropylbenzene desorbent itself may be used as para-cymene alone, or as 1-ethyl-4-isopropylbenzene alone, or as a mixture of para-cymene and 1-ethyl-4-isopropylbenzene.

The desorbent of the present invention may also be used with diluents such as saturated hydrocarbons, including the paraffinic type hydrocarbons and cycloparaffins. In one or more typical examples of the invention in which a diluent is used, such diluent may include straight or branched-chain paraffins. These include cycloparaffins such as cyclohexane, cyclopentane and branched derivatives thereof, as well as decalin and its branched-chain derivatives.

Suitable adsorbents include the aforementioned Otani et al crystalline aluminosilicates, the disclosure of Otani et al which explains the structure and makeup of such crystalline aluminosilicate adsorbents being incorporated herein by reference. In accordance with a preferred form of the present invention with respect to the adsorbents which are utilized in accordance with the invention, the crystalline aluminosilicate adsorbents are the faujasite type zeolites which are commonly represented as type X and Y zeolites, and are defined by varying silica to alumina ratios. Faujasite-type zeolites contain selected cations at the exchangeable cation sites. For the selective adsorption of para-xylene, these cations are preferably selected from the group consisting of Group IA, Group IIA, Group IB metal cations and proton.

A particularly advantageous faujasite-type zeolite in the process of this invention is one in which potassium cations are present, either alone or together with other cations selected from Group IA, Group IIA, Group IB, yttrium, lead, zirconium, neodymium, thallium, thorium or proton.

Referring to the drawing:

The drawing represents a schematic arrangement and flow diagram illustrating one specific embodiment of this invention, showing a fixed bed apparatus connected for countercurrent flow operations. This drawing is intended to be illustrative, and not to define or to limit the scope of the invention, which is defined in the claims.

Referring to the specific embodiment selected for illustration, which will be described in specific terms hereinafter without intending to limit the scope of the invention thereby, the apparatus comprises three zones, 1 being a desorption zone, 2 being a rectification zone, and 3 being an adsorption zone. Each zone comprises four columns which are charged with adsorbent. These zones are serially and circularly interconnected in order. In the desorption zone 1 in which the desorption step is conducted, para-xylene adsorbed on an adsorbent is displaced by contact with a desorbent stream, while simultaneously removing an extract stream comprising desorbent and para-xylene. In the rectification zone 2, the adsorbent in this zone is contacted with a reflux stream comprising para-xylene and desorbent to effect a purification of para-xylene and this stream is directed to maintain countercurrent operation against a simulated flow of the adsorbent.

In the adsorption zone 3, para-xylene is adsorbed on the adsorbent from a feed containing a mixture of $C_8$ aromatic hydrocarbons, with simultaneous removal of a raffinate stream which contains the less selectively adsorbed components of the feed, and desorbent.

The individual columns are serially and circularly connected to each other by means of a relatively small diameter connecting pipe fitted with a valve, and the valves 9 and 10 which are provided between the desorption zone and the rectification zone and between the adsorption zone and the desorption zone respectively are closed, while simultaneously all of the other valves not shown in FIG. 1 are opened.

Additionally, all columns are connected to a desorbent feed line 4, an extract withdrawal line 5, a reflux feed line 6, a feed inlet line 7, and a raffinate withdrawal line 8, wherein the individual connecting embodiment is not shown in detail in FIG. 1.

In operation, the top columns of the desorption, rectification and adsorption zones are simultaneously transferred to the bottoms of the adsorption, desorption and rectification zones, respectively, at predetermined time intervals. The transfer is effected by shifting all the points of introduction and withdrawal of all the lines into and from the one column simultaneously in a downstream direction. Thus, a simulated countercurrent flow system is provided achieving an effect similar to that of a moving bed type adsorption process. Therefore, the feed containing a mixture of C8 aromatic hydrocarbons may be continuously separated to produce both the selectively adsorbed component (i.e., para-xylene) and the less selectively adsorbed components (meta-xylene, ortho-xylene and ethylbenzene), respectively.

In accordance with the process of the present invention, the temperature should be from about zero to about 350° C., preferably about 30° C. to about 250° C. The pressure should be from about atmospheric pressure to about 40 kg/cm$^2$. Although in theory both liquid and vapor phase operations may be utilized for carrying out the separatory process of the present invention, it has been found preferably in practice to utilize a liquid phase separation because of the reduced temperature requirements and the possibility of suppressing the unwanted side reactions that may occur in the practice of high temperature operations.

In accordance with the process of the present invention the raffinate and the extract streams can be passed into different fractionating facilities, so that the extract stream may be separated to form a relatively pure desorbent stream and a relatively pure para-xylene stream. The raffinate stream can similarly be passed into a fractionating facility in which the raffinate material can be separated into a concentrated stream of desorbent material and another stream containing the less selectively adsorbed feed components. In accordance with the present invention the relatively purified desorbent stream from both the raffinate stream and the extract stream may be reused in the process of the invention.

The desorbent material which has been contacted with the adsorbent in the desorption step may be displaced by a part of the raffinate stream in advance of the adsorption step, in order to recover a relatively pure desorbent stream which may be reused in the process of the invention.

The adsorbent which has selectively adsorbed para-xylene in the adsorption step may be contacted with a part of the extract stream or an enriched para-xylene stream prior to the desorption step, in order to effect purification of the selectively adsorbed para-xylene.

The raffinate stream comprising the less selectively adsorbed components of the feed can be passed into an isomerization zone in which isomerization conditions take place to produce additional amounts of para-xylene. The combination of isomerization and separation processes thus allows the possibility of an increased yield of the desired para-xylene from the feed stock based upon the quantity of the C8 aromatic hydrocarbon feed.

In testing various desorbents in the following Examples, the selectivity of the adsorbent in the presence of desorbent was determined using a static testing apparatus, and using the procedures which are described in further detail hereinafter.

EXAMPLES

The static testing apparatus used in these Examples was a container having a volume of 5 ml and was made of stainless steel. 2 gm. of feed containing a mixture of C8 aromatic hydrocarbons and desorbent, and 2 gm. of adsorbent were introduced into the container. It was then stoppered and placed into an oil bath at a predetermined temperature for one hour, attaining an equilibrium adsorption state. The liquid in the apparatus was sampled for testing with a microsyringe, and was analyzed by means of gas chromatography. The selectivity (alpha) value for obtaining para-xylene, $\alpha$ px/x, was calculated according to the above equation.

The Examples which are set forth below illustrate particular embodiments of the invention, and are not intended as being other than exemplary, the invention being defined in the appended claims.

EXAMPLE 1

As the adsorbent, a crystalline potassium Y zeolite was used, which was prepared by the following method. The sodium form of type Y zeolite, which consisted of 4.8 mole ratio of silica over alumina, was subjected to ion exchange treatment in which the zeolite was contacted with 5 wt. percent potassium nitrate aqueous solution until the residual sodium cations dropped to less than 20 percent, based on the total amount of cations within the zeolite. After completing the ion exchange treatment, the zeolite was dried at 120° C. for three hours and was then calcined at 500° C. for three hours.

In order to evaluate the performance of para-cymene or 1-ethyl 4-isopropylbenzene as desorbent materials in the process of the present invention, the selectivity for para-xylene was determined at 30° C. by the procedure previously described above.

The feed mixture used for this test had the following composition:

| | |
|---|---|
| Meta-xylene | 1 part by weight |
| Normal nonane (n-C9) | 1 part by weight |
| Para-xylene (px) | 1 part by weight |
| Ortho-xylene (ox) | 1 part by weight |
| Ethylbenzene (eb) | 1 part by weight |
| Para-cymene (pcm) | 1 part by weight |
| or | |
| 1-Ethyl-4-iso-propylbenzene (eipb) | 1 part by weight |

It was assumed in carrying out this test that the n-C9 was not adsorbed within the adsorbent. Accordingly, the selectivities were calculated using the above equation. The results are set forth in Table 1.

TABLE 1

| EX. NO. | 1 | 1 | 2 |
|---|---|---|---|
| Desorbent | para-cymene | 1-ethyl-4-isopropyl-benzene | para-diethyl-benzene |
| Selectivity ($\alpha$) for: | | | |
| $\frac{px}{eb}$ | 1.9 | 2.2 | 1.5 |
| $\frac{px}{mx}$ | 5.5 | 6.1 | 4.1 |
| $\frac{px}{ox}$ | 5.3 | 5.9 | 4.1 |

EXAMPLE 2

To compare the present invention with the prior art, a comparison was made with para-diethylbenzene (p-deb), which was considered in the prior art literature to be the preferred desorbent for this purpose.

The adsorbent prepared in accordance with Example 1 was contacted with a feed mixture having the following ratio in terms of weight:

n-C9:px:mx:ox:eb:p-deb = 1:1:1:1:1:1, namely, one part by weight of each of the above components was present.

The other conditions used in the present Example were in accordance with Example 1. The results of this Example 2 are also set forth in Table 1.

It will also be noted from Table 1 that the most difficult component to separate from para-xylene is ethylbenzene. Accordingly, this selectivity value is of greatest importance.

Table 1 shows that each desorbent of the present invention provides a higher alpha value for para-xylene versus ethylbenzene than para-diethylbenzene.

EXAMPLE 3

The same adsorbent as in Example 1 was contacted with a feed of the following composition, the other parameters of Example 1 being followed except that a temperature of 170° C. was used:

n-C9 : px : mx : ox : eb : desorbent = 1 : 1 : 1 : 1 : 1: 5

The results are tabulated at Table 2.

TABLE 2

| EX. NO. | 3 | 3 | 4 | 5 |
|---|---|---|---|---|
| Desorbent | para-cymene | 1-ethyl-4-isopropylbenzene | mixture of para-cymene and para-diethylbenzene | para-diethylbenzene |
| Selectivity (α) for: | | | | |
| $\frac{px}{eb}$ | 2.0 | 2.1 | 1.9 | 1.8 |
| $\frac{px}{mx}$ | 3.1 | 3.8 | 3.1 | 3.0 |
| $\frac{px}{ox}$ | 2.7 | 3.3 | 2.8 | 2.8 |

EXAMPLE 4

As desorbent, a mixture of 50% para-cymene and 50% para-diethylbenzene was used, based upon the weight of the components. The other test conditions were the same as used in Example 3.

The results are set forth in Table 2 (see col. 4).

EXAMPLE 5

As desorbent, para-diethylbenzene was used. The adsorbent prepared in Example 1 was contacted with a feed mixture having the following composition:

n-C9:px:mx:ox:eb:p-deb = 1:1:1:1:1:5

The other conditions were the same as in Example 3. The results are set forth in Table 2 (see col. 5).

A superior selectivity for the para-xylene versus ethylbenzene can be seen for the desorbents of the present invention.

EXAMPLE 6

In this Example, para-cymene was demonstrated to be an effective desorbent for separation of para-xylene from a mixture of C8 aromatic hydrocarbons.

The apparatus utilized was that set forth in FIG. 1, which was a fixed bed apparatus through which fluid flow was directed to maintain countercurrent flow operations which simulated a moving bed type operation, as previously described herein.

In the present Example, each of the columns (which had an inner diameter of 25 mm and a height of 2.0 m) was fully packed with potassium zeolite Y adsorbent (12-24 mesh) which was prepared in accordance with Example 1. Opening and closing of all the valves was effected by a time-actuated automatic control appratus, and the shift interval was programmed for 3.5 minutes.

A feed stock consisting of 20% para-xylene, 40% meta-xylene, 20% ortho-xylene, and 20% ethylbenzene (each component by weight) was, after heating to 165° C., continuously fed through line 7 at a flow rate of 4.0 kg/hour and under a pressure of 8 kg/cm$^2$ gage.

A reflux stock consisting of 90% para-xylene and 10% para-cymene (by weight) that had been previously prepared was heated to 165° C. and continuously fed through line 6 at a flow rate of 25.7 kg/hour and a pressure of 10 kg/cm$^2$ gage.

Para-cymene was provided as the desorbent material and was, after heating to 165° C., continuously fed through line 4 at a flow rate of 32.0 kg/hour and at a pressure of 12 kg/cm$^2$ gage.

An extract stream was continuously withdrawn through line 5, in which stream para-xylene was present at an average concentration of 74.6% by weight based on the total stream. After para-cymene was separated from the extract by distillation, the para-xylene fraction had a purity of 99.4% by weight. In the raffinate stream, para-xylene was present at an average concentration of 0.2% by weight based on the total stream.

EXAMPLE 7

The Example shows that pure para-xylene was separated effectively from a mixture of C8 aromatic hydrocarbons when 1-ethyl-4-isopropylbenzene was emplyed as the desorbent.

The apparatus and conditions were the same as in Example 6, except as described below.

A reflux stock consisting of 90% para-xylene and 10% previously prepared 1-ethyl-4-isopropylbenzene by weight was continuously fed at a flow rate of 25.1 kg/hour.

1-ethyl-4-isopropylbenzene as desorbent material was continuously fed at a flow rate of 34.4 kg/hour. The shift interval was programmed for 3.2 minutes.

In the extract stream, para-xylene was present at an average concentration of 67.9% by weight, based upon the total stream. After 1-ethyl-4-isopropylbenzene was separated from the extract by distillation, the para-xylene fraction had a purity of 99.4% by weight. In the raffinate stream, para-xylene was present at an average concentration below 0.2% by weight, based on the total stream.

Although this invention has been described with reference to particular apparatus for carrying the process into effect, a variety of different forms of apparatus, and many different manipulative steps may be used, all taking advantage of the basic discovery that the 1-lower alkyl-4-isopropylbenzenes (alkyl being methyl or ethyl)

have surprising effectiveness in the desorptive enrichment of C$_8$ hydrocarbons. For example, the process is not limited to utilizing the three-zone system described in the Examples, or to simultaneous shifting of points of introduction or withdrawal of streams. Any of the various known techniques or equipment for solids-fluid contacting operations may be used for either the adsorption step or the desorption step, or both, such as a compact moving bed, for example, passed successively through the adsorption and desorption operations with co-current or countercurrent contact with the streams, fluids or vapors. Accordingly, it will be appreciated that equivalents may be substituted, that certain features may be used independently of others, and that steps may be reversed, all without departing from the spirit and scope of the invention as defined in the appended claims.

We claim:

1. A process for enrichment of para-xylene content in a feed containing a mixture of C$_8$ aromatic hydrocarbons including para-xylene, which process comprises:
    (a) passing said feed into contact with a crystalline adsorbent capable of selectively adsorbing para-xylene from said feed, thereby adsorbing a greater percentage of para-xylene than other components of said feed on said adsorbent;
    (b) desorbing para-xylene from said crystalline adsorbent by contacting said crystalline adsorbent with a desorbent containing a 1-(lower alkyl)-4-isopropylbenzene, wherein the lower alkyl group contains 1–2 carbon atoms; and
    (c) removing a mixture containing a 1-(lower alkyl)-4-isopropylbenzene and para-xylene from said adsorbent.

2. A process of claim 1, wherein said 1-(lower alkyl)-4-isopropylbenzene is para-cymene.

3. A process of claim 1, wherein said 1-(lower alkyl)-4-isopropylbenzene is 1-ethyl-4-isopropylbenzene.

4. The process of claim 1, wherein said adsorbent is a crystalline aluminosilicate adsorbent.

5. The process of claim 4, wherein said crystalline aluminosilicate adsorbent is a faujasite-type zeolite.

6. The process of claim 5, wherein said faujasite-type zeolite contains potassium cations at the cation exchangeable sites.

7. The process of claim 5, wherein said faujasite-type zeolite contains potassium cations and at least an additional cation selected from Group IA other than potassium, Group IIA, Group IB, yttrium, lead, zirconium, neodymium, thallium and thorium cations and proton at the cation exchangeable sites.

8. A process for desorbing para-xylene from a crystalline adsorbent which comprises contacting said crystalline adsorbent with a 1-(lower alkyl)-4-isopropylbenzene, wherein the lower alkyl group contains 1–2 carbon atoms, and removing the resulting mixture from said adsorbent.

9. The process of claim 8, wherein said 1-(lower alkyl)-4-isopropylbenzene is p-cymene.

10. The process of claim 8, wherein said 1-(lower alkyl)-4-isopropylbenzene is 1-ethyl-4-isopropylbenzene.

11. The process of claim 8, wherein said adsorbent is a crystalline aluminosilicate adsorbent.

12. Desorbing para-xylene from an adsorbent by contacting it with a desorbent selected from the group consisting of para-cymene and 1-ethyl-4-isopropylbenzene.

13. A continuous process for the separation of para-xylene from a feed stream containing a mixture of C$_8$ aromatic hydrocarbons including para-xylene, which process comprises:
    (a) passing said feed into contact with a crystalline adsorbent capable of selectively adsorbing para-xylene from said feed, thereby adsorbing a greater percentage of para-xylene than other components of said feed on said adsorbent;
    (b) desorbing para-xylene from said crystalline adsorbent by contacting said crystalline adsorbent with 1-(lower alkyl)-4-isopropylbenzene, wherein the lower alkyl group contains 1–2 carbon atoms, and a diluent,
    (c) removing a mixture containing said 1-(lower alkyl)-4-isopropylbenzene, para-xylene and diluent from said adsorbent, and
    (d) separating para-xylene from said mixture.

14. The process of claim 13, wherein said adsorbent is a crystalline aluminosilicate adsorbent.

15. In an adsorptive-separation process for the separation of para-xylene from a feed stream containing a mixture of C$_8$ aromatic hydrocarbons including para-xylene by passing said feed stream into contact with a crystalline aluminosilicate adsorbent capable of selectively adsorbing para-xylene from said feed stream, the improvement which comprises desorbing para-xylene from said adsorbent by contacting said adsorbent with a desorbent containing 1-(lower alkyl)-4-isopropylbenzene, wherein the lower alkyl group contains 1–2 carbon atoms.

16. The process of claim 15, wherein said 1-(lower alkyl)-4-isopropylbenzene is para-cymene.

17. The process of claim 15, wherein said 1-(lower alkyl)-4-isopropylbenzene is 1-ethyl-4-isopropylbenzene.

18. The process of claim 15, wherein said adsorbent is a faujasite-type zeolite.

19. A process for separating para-xylene from a feed stream of C$_8$ aromatic hydrocarbons including para-xylene from a system containing a desorption zone, a rectification zone and an adsorption zone, each of said zones being charged with an aluminosilicate adsorbent, which comprises:
    (a) passing said feed stream into said adsorption zone so as to adsorb said para-xylene on said adsorbent and simultaneously removing a raffinate stream of less selectively adsorbed components of the feed stream and said desorbent;
    (b) contacting the adsorbent in said rectification zone with a reflux stream of an extract to effect purification of para-xylene and to maintain countercurrent operation against a simulated flow of the adsorbent, and
    (c) passing a desorbent stream containing 1-(lower alkyl)-4-isopropylbenzene into said desorption zone and simultaneously removing an extract stream of desorbent and para-xylene.

20. The process of claim 19, wherein said desorbent contains a 1-(ethyl)-4-isopropylbenzene.

21. The process of claim 19, wherein said desorbent contains a para-cymene.

* * * * *

UNITED STATES PATENT AND TRADEMARK OFFICE
CERTIFICATE OF CORRECTION

PATENT NO. : 4,139,572
DATED : February 13, 1979
INVENTOR(S) : Kishio Miwa et al It is certified that error appears in the above-identified patent and that said Letters Patent are hereby corrected as shown below:

Column 1, line 21, "containing" should read -- contains --.

Signed and Sealed this

Twenty-sixth Day of June 1979

[SEAL]

Attest:

RUTH C. MASON
Attesting Officer

DONALD W. BANNER
Commissioner of Patents and Trademarks